United States Patent [19]

Saito et al.

[11] Patent Number: 5,494,665
[45] Date of Patent: Feb. 27, 1996

[54] MAN-MADE SALIVA FLUIDS

[75] Inventors: Noriko Saito, Minoo; Kenichi Yoshida; Fuminori Tokumochi, both of Kobe, all of Japan

[73] Assignee: Senju Pharmaceutical Co., Ltd., Osaka, Japan

[21] Appl. No.: 143,788

[22] Filed: Nov. 1, 1993

[30] Foreign Application Priority Data

Nov. 2, 1992 [JP] Japan .................................. 4-317803

[51] Int. Cl.$^6$ .............................. A61K 7/28; A61K 38/43; A61K 47/38

[52] U.S. Cl. ...................... 424/94.61; 424/50; 424/680; 514/781; 514/900

[58] Field of Search ............................ 424/49–58, 94.61, 424/680; 514/781, 900

[56] References Cited

U.S. PATENT DOCUMENTS 4,820,506  4/1989  Kleinberg et al. .................... 424/40
4,879,281 11/1989  Shibaskai et al. .
5,147,648  9/1992  Bannert .................................. 424/435
5,260,282 11/1993  Attstrom et al. .......................... 514/54

FOREIGN PATENT DOCUMENTS 0511181 10/1982 European Pat. Off. .
4113684 10/1992 Germany .

OTHER PUBLICATIONS

Derwent Publications Ltd., AN 77–75174Y of Toyama I JPN 52/08013 Sep. 10, 1977 cellulose thickness!Derwent Publications Ltd., AN 77–75175Y of Toyama II JPN 52/08014 Sep. 10, 1977 lysozyme!!

*Primary Examiner*—Shep K. Rose
*Attorney, Agent, or Firm*—Foley & Lardner

[57] ABSTRACT

The present invention provides man-made saliva fluids which contain lysozyme chloride in such concentrations as may be able to suppress effectively the development of oral edema and which possess improved feeling of use and show lessened change in appearance and pH value as well as minimized reduction in enzymatic activity of lysozyme chloride after a prolonged period of storage.

10 Claims, No Drawings

MAN-MADE SALIVA FLUIDS

There have been proposed and put on the market a great variety of artificial or man-made saliva fluids intended for application to saliva deficiency caused by damage to the oral cavity. For example, there have been published man-made saliva fluids which individually comprise the required inorganic salts and the following specific ingredient(s): mucin added as a thickening agent (The Japanese Patent Application Laid-Open No. 57-500562); salts of arginic acid, etc. or pectin and sorbit being formulated as a thickening agent (The Japanese Patent Application Laid-Open No. 57-502186); hydroxypropylcellulose, methylcellulose or hydroxypropylmethylcellulose being incorporated as a thickening agent and sodium guaiazulenesulfonate being added as a bactericide (The Japanese Patent Application Laid-Open No. 59-7116 and 59-27818); an alkali salt of carboxymethylcellulose with an etherification degree of not less than 150 being incorporated as a thickening agent (The Japanese Patent Application Laid-Open No. 61-151118); an aqueous solution of a thread-trailing polymer such as polyacrylic acids being formulated as a thickening agent and sorbitol, xylitol, polyglycerol, glycerol, etc. being admixed as a humectant (The Japanese Patent Application Laid-Open No. 62-236862); a phosphate buffer contained (The Japanese Patent Publication No. 55-26121); and, digestive enzymes, hormones, lysozyme or antimicrobial agents, phosphate buffer and thickening agent being admixed (The Japanese Patent Publication No. 55-26122). In the above-described Japanese Patent Application Laid-Open No. 62-236862, glycerol is used at a concentration of 5%, while the Japanese Patent Publication No. 55-26122 gives the description that lysozyme chloride is preferably added at a rate of 0.5 to 2 g/L.

Nevertheless, such salivary preparations are considered far from being fully satisfactory in terms of storage stability, feeling of use, mucosa-irritation, antimicrobial or bacteriostatic property, etc.

The present inventors, with a specific view to the development of the improved man-made saliva fluid, have conducted repeatedly extensive research for a long period of time, thus leading to the establishment of the present invention.

The present invention relates to man-made saliva fluids having their pH values adjusted to about 5 to 6 which comprise the metal ions in the saliva contained in the form of chlorides as well as about 0.2 to 0.6% w/v of lysozyme chloride and an isotonic agent, non-ionic thickening agent and preservative contained therein.

In light of the fact that saliva contains potassium, sodium, magnesium and calcium ions, the present invention comprises the said metal ions being incorporated into the salivary preparation in the form of chlorides, or potassium chloride, sodium chloride, magnesium chloride and calcium chloride.

Referring to the concentration of each chloride in the salivary preparation, it is desirable to adjust potassium chloride, sodium chloride, magnesium chloride and calcium chloride to the proportions of about 0.1 to 0.2% w/v, 0.03 to 0.2% w/v, 0.0007 to 0.008% w/v, and 0.01 to 0.02% w/v, respectively.

Lysozyme chloride is contained in the salivary preparation of the present invention at a concentration of not less than about 0.2% w/v but up to 0.6% w/v. The present inventors, after their research work, found that lysozyme chloride at a concentration of 0.2% w/v exhibits an inhibitory rate against edema in the oral cavity in the proximity to 50%, which inhibitory rate grows with increasing concentration, although the enzyme at a concentration of 0.1% w/v shows merely about 25% of the inhibitory rate. This finding has culminated into the discovery that lysozyme chloride would desirably be used at the concentration of about 0.2 to 0.6% w/v (refer to Reference Example 1).

The salivary preparation of the present invention is adjusted to a pH value in the range of about 5 to 6 with an alkali hydroxide or alkali citrate.

Since lysozyme chloride in the salivary preparation is likely to undergo deactivation during storage, the present inventors conducted an investigation into the correlation between its storage stability and its used buffer or pH value, and found that lysozyme chloride is stabilized by simply adjusting the pH of the salivary preparation to 5 to 6 with an alkali hydroxide or alkali citrate, thus eliminating the need to utilize a buffer such as a phosphate buffer (refer to Reference Example 2).

As a preservative in the salivary preparation of the present invention, it is preferable to use p-oxybenzoates such as methyl p-oxybenzoate and cationic surfactants such as benzalkonium chloride and cetylpyridinium chloride. (refer to Reference Example 3).

Because the addition of inorganic salts as an isotonic agent breaks the ion balance, it is preferred to employ polyhydric alcohols such as sorbitol, concentrated glycerol and propylene glycol (refer to Reference Example 4).

As a thickening agent in the salivary preparation of the present invention, there are added non-ionic thickening agents such as hydroxypropyl methylcellulose or hydroxypropylcellulose and methylcellulose, with their concentrations preferably ranging from about 0.3 to 0.5% w/v to secure the better feeling of use (refer to Reference Example 5).

The salivary preparation of the present invention was found to be free from any abnormalities in the mucosa irritation test through instillation into the eyes of rabbits, with no irritating property being observed.

The salivary preparation of the present invention, after being stored at 40° C. for 6 months or at room temperature for 12 months, showed no change in appearance, pH or residual rate of lysozyme chloride, and remained stable.

The salivary preparation of the present invention can be used effectively in the treatment of xerostomia, without accompaniment of particular side effects.

The examples and reference examples are described in the following to further illustrate the present invention.

EXAMPLE 1

| Material | Weight, g |
| --- | --- |
| Lysozyme chloride | 0.2 |
| Potassium chloride | 0.15 |
| Sodium chloride | 0.09 |
| Magnesium chloride | 0.005 |
| Calcium chloride | 0.001 |
| Hydroxypropyl methylcellulose | 0.1 |
| Sorbitol | 4.2 |
| Benzalkonium chloride | 0.005 |
| Perfume | Appropriate amount |

The above materials were dissolved in purified water to make up to 100 ml, and the resultant solution was adjusted to a pH 5.5 with sodium hydroxide.

EXAMPLE 2

| Material | Weight, g |
| --- | --- |
| Lysozyme chloride | 0.3 |
| Potassium chloride | 0.12 |
| Sodium chloride | 0.06 |
| Magnesium chloride | 0.005 |
| Calcium chloride | 0.001 |
| Hydroxypropyl methylcellulose | 0.3 |
| Glycerol | 2.0 |
| Cetyl pyridinium chloride | 0.005 |
| Perfume | Appropriate amount |

The above materials were dissolved in purified water to make up to 100 ml, and the resultant solution was adjusted to a pH 6.0 with sodium citrate.

EXAMPLE 3

| Material | Weight, g |
| --- | --- |
| Lysozyme chloride | 0.4 |
| Potassium chloride | 0.13 |
| Sodium chloride | 0.085 |
| Magnesium chloride | 0.004 |
| Calcium chloride | 0.001 |
| Hydroxypropyl methylcellulose | 0.2 |
| Glycerol | 2.0 |
| Methyl p-oxybenzoate | 0.1 |
| Perfume | Appropriate amount |

The above materials were dissolved in purified water to make up to 100 ml, and the resultant solution was adjusted to a pH 5.0 with sodium hydroxide.

EXAMPLE 4

| Material | Weight, g |
| --- | --- |
| Lysozyme chloride | 0.2 |
| Potassium chloride | 0.1 |
| Sodium chloride | 0.06 |
| Magnesium chloride | 0.004 |
| Calcium chloride | 0.0015 |
| Methylcellulose | 0.1 |
| Glycerol | 2.0 |
| Chlorohexidine gluconate | 0.005 |
| Perfume | Appropriate amount |

The above materials were dissolved in purified water to make up to 100 ml, and the resultant solution is adjusted to a pH 6.0 with sodium hydroxide.

EXAMPLE 5

| Material | Weight, g |
| --- | --- |
| Lysozyme chloride | 0.2 |
| Potassium chloride | 0.1 |
| Sodium chloride | 0.06 |
| Magnesium chloride | 0.004 |
| Calcium chloride | 0.0015 |
| Hydroxypropylcellulose | 0.3 |
| Glycerol | 2.0 |
| Chlorohexidine gluconate | 0.005 |
| Perfume | Appropriate amount |

The above materials were dissolved in purified water to make up to 100 ml, and the resultant solution was adjusted to a pH 6.0 with sodium hydroxide.

EXAMPLE 6

| Material | Weight, g |
| --- | --- |
| Lysozyme chloride | 0.3 |
| Potassium chloride | 0.15 |
| Sodium chloride | 0.06 |
| Magnesium chloride | 0.005 |
| Calcium chloride | 0.015 |
| Hydroxypropylcellulose | 0.1 |
| Glycerol | 2.0 |
| Benzethonium chloride | 0.005 |
| Perfume | Appropriate amount |

The above materials were dissolved in purified water to make up to 100 ml, and the resultant solution was adjusted to a pH 5.0 with sodium hydroxide.

REFERENCE EXAMPLE 1

Test on the inhibition of edema in the mucosa of the oral cavity by spraying a solution of lysozyme chloride

Test material

Lysozyme chloride solutions in isotonic saline having the concentrations of 0.05% w/v, 0.1% w/v, 0.2% w/v and 0.4% w/v were employed as a test material, with isotonic saline being used as a control.

Test method

Male Wistar rats weighing about 150 g, as divided into 5 groups each consisting of 6 heads, were subjected to the experiment; the rats were treated through spraying over their oral-cavity mucosas a 20 µl portion each of 0.04% w/v, 0.2% w/v, 0.1% w/v and 0.05% w/v lysozyme-chloride solutions and isotonic saline three times at a regular interval of 30 min. Thirty minutes after the last spraying treatment, 0.5 ml of 0.5% w/v Evans blue was injected into the tail vein of each rat, followed by instantaneous injection of 30 µl of 1% w/v carrageenin beneath the oral mucosa to cause inflammation. One hour later, each rat was sacrificed through dislocation of the cervical vertebrae, and the edema portion in the oral mucosa having the dye leaked was incised and cut to pieces, which were left on standing in 10 ml of formamide at 37 C. one day to extract the dye. The extract was subjected to measurement of the absorbance at a wavelength of 625 nm, and the edema inhibition rate was calculated for each rat group by the following equation:

$$I = (1 - At/Ac) \times 100$$

where:

$I$ = Edema inhibition rate, %

$At$ = Mean absorbance for the test group $Ac$ = Mean absorbance for the control group It is to be noted that 20 µl as a given volume of the test material corresponds to a volume remaining in the oral cavity when a human uses 100 ml of a gargle.

Results

Shown in Table 1 are the absorbances and edema-inhibition rates for the respective rat groups:

TABLE 1

| Test material | Absorbance ± S.D. | Inhibition rate | No. of animals |
|---|---|---|---|
| Isotonic saline | 0.312 ± 0.048 | — | 6 |
| 0.05% Lz | 0.271 ± 0.066 | 13.1% | 6 |
| 0.1% Lz | 0.233 ± 0.030 | 25.3% | 6 |
| 0.2% Lz | 0.164 ± 0.030 | 47.4% | 6 |
| 0.4% Lz | 0.137 ± 0.028 | 56.1% | 6 |

Note: The symbol "Lz" designates "lysozyme chloride".

As can be seen from the above, 0.1% w/v lysozyme chloride solution produced a significant difference from isotonic saline in terms of edema inhibition rate, but showed a lowered edema inhibition rate. On the other hand, 0.2% w/v lysozyme chloride solution exhibited an edema-inhibition rate as high as 47.4%, whereby the edema inhibition rate displayed a tendency to grow with the increasing concentration of lysozyme chloride. Consequently, the above suggests that the concentration of lysozyme chloride of 0.2% w/v or in excess thereof is suitable for the preparation.

REFERENCE EXAMPLE 2

Test on the storage stabilities of the salivary preparations at different pH values
1) Test material
As a test material, there were used the preparations of the following formulations:

| Material | Rp. 1 | Rp. 2 |
|---|---|---|
| Lysozyme chloride | 0.2 % w/v | " |
| Potassium chloride | 0.12 | " |
| Sodium chloride | 0.085 | " |
| Magnesium chloride | 0.005 | " |
| Calcium chloride | 0.015 | " |
| Sodium hydrogenphosphate | 0.03 | — |
| Sodium citrate | — | 0.03 |
| Hydrochloric acid | Appropriate | " |
| Sodium hydroxide | Appropriate | " |
| Purified water | Appropriate | " |

2) Test method
The salivary preparations of different formulations were adjusted to individually varied pH values of 5, 6, 7 and 8, and stored at 50° C. for 6 weeks, followed by measurement of pH values and residual rates of lysozyme chloride (the contents of lysozyme chloride were measured in accordance with the procedure as set forth in Code Outside Japanese Pharmacopeia).
3) Results
The results are shown in Table 2:

TABLE 2

Storage stabilities of the salivary preparations at different pH values (at 50° C.).

| Rp | Item | pH 5 Before | pH 5 After | pH 6 Before | pH 6 After | pH 7 Before | pH 7 After | pH 8 Before | pH 8 After |
|---|---|---|---|---|---|---|---|---|---|
| 1 | pH | 5.01 | 5.25 | 6.07 | 6.23 | 7.02 | 7.46 | 8.04 | 7.76 |
|   | Res. rate, % | 100 | 100 | 100 | 101 | 100 | 44 | 100 | 72 |
| 2 | pH | 5.11 | 5.36 | 6.08 | 6.68 | 7.00 | 7.41 | 7.98 | 7.62 |
|   | Res. rate, % | 100 | 100 | 100 | 94 | 100 | 84 | 100 | 72 |

Note: "Res. rate" designates "residual rate".

4) Discussions

Referring to the storage stability at different pH values, as shown in Table 2, both of the formulations Rp 1 and Rp 2 with their pH values adjusted at 5 and 6, after storage at 50° C. for 6 weeks, showed a slight increase in pH but displayed almost no change in the residual rate of lysozyme chloride, whereas the preparations of pH 7 and 8 exhibited marked decreases in the residual rate of lysozyme chloride. In consequence, it is considered desirable to have the salivary preparation adjusted to a pH in the neighborhood of 5 and 6 when it comes to assurance of its stability. No difference was noted with the varied types of buffers, and based on the finding that buffers at the used concentrations failed to develop adequate buffering action, it is thought unnecessary to formulate buffers into the salivary preparation.

REFERENCE EXAMPLE 3

Test on the storage stabilities of the salivary preparations incorporated with various preservatives:
1) Test material
As a test material, there were used the preparations of the following formulations:

| Material | Rp. 3 | Rp. 4 | Rp. 5 | Rp. 6 |
|---|---|---|---|---|
| Lysozyme chloride | 0.2 % w/v | " | " | " |
| Potassium chloride | 0.12 | " | " | " |
| Sodium chloride | 0.085 | " | " | " |
| Magnesium chloride | 0.005 | " | " | " |
| Calcium chloride | 0.015 | " | " | " |
| Sorbic acid | 0.05 | — | — | — |
| Methyl p-oxybenzoate | — | 0.1 % w/v | — | — |
| Benzalkonium chloride | — | — | 0.005 % w/v | — |
| Cetylpyridinium chloride | — | — | — | 0.005 % w/v |
| Hydrochloric acid | Appropriate | " | " | " |
| Sodium hydroxide | Appropriate | " | " | " |
| Purified water | Appropriate | " | " | " |

2) Test method
Each of the salivary preparations of the different formulations were subjected to pH adjustment and stored at 60° C. for 5 weeks, followed by determination of appearance, pH and residual rate of lysozyme chloride.
3) Results
The results are shown in Table 3.

TABLE 3

Storage stability of the salivary preparations with pH 5 (effects of preservatives)

| Rp. | Item | Before | After |
|---|---|---|---|
| 3 | Appearance | Colorless, clear | Yellowish precipitate |
|   | pH | 5.03 | 5.04 |
|   | Res. rate. % | 100 | 44 |
| 4 | Appearance | Colorless, clear | No change |
|   | pH | 5.03 | 5.10 |
|   | Res. rate. % | 100 | 73 |
| 5 | Appearance | Colorless, clear | No change |
|   | pH | 5.00 | 5.26 |
|   | Res. rate. % | 100 | 65 |
| 6 | Appearance | Colorless, clear | No change |
|   | pH | 4.99 | 5.06 |
|   | Res. rate. % | 100 | 57 |

Note: "Res. rate" designates "residual rate".

As is evident from Table 3, sorbic acid used as a preservative gave rise to a change in appearance, along with a marked reduction in residual rate of lysozyme chloride, whereas methyl p-oxybenzoate, benzalkonium chloride and cetylpyridinium chloride utilized as a preservative did not produce any change in appearance and brought about a slight decrease in residual rate.

REFERENCE EXAMPLE 4

Test on the taste and flavor of the salivary preparations formulated with various isotonic agents Investigation was conducted into the taste and flavor of the principal ingredients for the man-made saliva fluid as well as the effects of isotonic agents on the taste and flavor.

1) Test material

As a test material, there were used the preparations of the following formulations:

| Ingredient | Rp. 7 | Rp. 8 | Rp. 9 | Rp. 10 |
|---|---|---|---|---|
| Lysozyme chloride | 0.2 % w/v | " | " | " |
| Potassium chloride | 0.12 | " | " | " |
| Sodium chloride | 0.085 | " | " | " |
| Magnesium chloride | 0.005 | " | " | " |
| Calcium chloride | 0.015 | " | " | " |
| Sorbitol | 4.2 % w/v | — | — | — |
| Conc. glycerol | — | 2.0 % w/v | — | — |
| Propylene glycol | — | — | 1.4 % w/v | — |
| Purified water | Appropriate | " | " | " |

Note: Sorbitol, concentrated glycerol and propylene glycol were added to confer isotonicity to the preparations.

2) Test method

Salivary preparations of the different formulations were examined for the taste and flavor.

3) Results

The results are tabulated in Table 4.

TABLE 4

Effects of various isotonic agents on the taste and flavor of the salivary preparation

| Formulation | Feeling of use (taste and flavor) |
|---|---|
| Rp. 7 | Initially felt sweet, leaving sweet aftertaste and astringent sensation as well. |
| Rp. 8 | Initially not felt sweet, yet leaving sweet aftertaste and astringent sensation. |
| Rp. 9 | Initially felt bitter, leaving sweet aftertaste and astringent sensation. |
| Rp. 10 | Initially felt a little bit hot, yet leaving sweet aftertaste and astringent sensation. |

Because addition of inorganic salts causes break-down of the ion balance, investigation was conducted on the flavoring property of polyhydric alcohols which possess the combination of moisturizing and isotonic effects, when used to make the preparations isotonic. As a result, it turned out that none of sorbitol, concentrated glycerol and propylene glycol would cause any problem or disadvantage, as shown in Table 4.

REFERENCE EXAMPLE 5

Test on the effects of the non-ionic thickening agents on the feeling of use

Investigation was conducted on the effects of the concentration and viscosity of non-ionic thickening agents on the feeling of use 1) Test material AS a test material, there was used the preparation of the following formulation:

| Ingredient | Rf 11 |
|---|---|
| Lysozyme chloride | 0.2 % w/v |
| Potassium chloride | 0.12 |
| Sodium chloride | 0.085 |
| Magnesium chloride | 0.005 |
| Calcium chloride | 0.015 |
| Hydroxypropyl methylcellulose (90 SH 4000) | 0–0.5 % w/v |
| Conc. glycerol | 2.0 % w/v |
| Methyl paraben | 0.1 |
| Hydrochloric acid | Appropriate |
| Purified water | Appropriate |

2) Test method

The salivary preparations were prepared by using hydroxypropyl methylcellulose at different concentrations of 0, 0.1, 0.2, 0.3 and 0.5% w/v. and examined for viscosity (with use of Uberode viscometer) and feeling of use.

3) Results

Effects of various thickening agents on the feeling of use

| Concn., % | Viscosity, cSt | Feeling of use |
|---|---|---|
| 0 | 1 | Felt simple, leaving however the astringent sensation. |
| 0.1 | 2.4 | Felt unsatisfactory, leaving slightly mitigated astringent sensation. |
| 0.2 | 4.5 | Felt unsatisfactory, leaving slightly mitigated astringent sensation. |
| 0.3 | 9.0 | Viscous, making the oral cavity smooth and leaving mitigated astringent sensation. |
| 0.5 | 26 | Viscous, making the oral cavity smooth and leaving mitigated |

| Effects of various thickening agents on the feeling of use | | |
|---|---|---|
| Concn., % | Viscosity, cSt | Feeling of use |
| | | astringent sensation. |

4) Discussion

Incorporation of a thickening agent into the man-made saliva fluid is effective to make the oral cavity moist and smooth and to retain the moisturizing effect. Nevertheless, sodium carboxymethyl cellulose, when formulated into a salivary formulation incorporated with lysozyme chloride, caused turbidity and is not considered appropriate to be formulated. In view of this, testing was conducted with use of hydroxypropyl methylcellulose, a non-ionic thickening agent. As is shown in Table 5, the viscosity increases with the increasing concentration of the compound formulated, and as a result, the resulting viscosity exerted its physical action to thereby provide the salivary preparation with the cushioning property and consequently the improved feeling of use.

We claim:

1. A man-made saliva fluid having its pH value adjusted to about 5 to 6 with an alkali citrate or alkali hydroxide which comprises metal ions contained in the form of chlorides as well as about 0.3 to 0.6% w/v of lysozyme chloride and an isotonic agent, non-ionic thickening agent and preservative.

2. A man-made saliva fluid according to claim 1, wherein the metal ions are in the form of potassium chloride, sodium chloride, magnesium chloride and calcium chloride.

3. A man-made saliva fluid according to claim 1, wherein the isotonic agent is a polyhydric alcohol.

4. A man-made saliva fluid according to claim 3, wherein the polyhydric alcohol is glycerol, sorbitol, propylene glycol or mixtures thereof.

5. A man-made saliva fluid according to claim 1, wherein the non-ionic thickening agent is a hydroxy-lower-alkylcellulose or methylcellulose.

6. A man-made saliva fluid according to claim 5, wherein the hydroxy lower-alkylcellulose is hydroxypropylcellulose or hydroxypropylmethylcellulose.

7. A man-made saliva fluid according to claim 1, wherein the alkali citrate is sodium citrate.

8. A man-made saliva fluid according to claim 1, wherein the alkali hydroxide is sodium hydroxide.

9. A man-made saliva fluid according to claim 1, wherein said amount of lysozyme chloride is about 0.3% w/v.

10. A man-made saliva fluid according to claim 1, wherein said amount of lysozyme chloride is about 0.4% w/v.

* * * * *